United States Patent
Birkbeck et al.

(10) Patent No.: US 10,849,765 B2
(45) Date of Patent: Dec. 1, 2020

(54) IMPACTOR

(71) Applicant: DEPUY IRELAND UNLIMITED COMPANY, County Cork (IE)

(72) Inventors: Alec Birkbeck, Leeds (GB); Graeme Dutton, Burney (GB); David Horne, Leeds (GB); Thomas Maack, Batley (GB); Gary Moore, Wetherby (GB)

(73) Assignee: DEPUY IRELAND UNLIMITED COMPANY

( * ) Notice: Subject to any disclaimer, the term of this patent is extended or adjusted under 35 U.S.C. 154(b) by 11 days.

(21) Appl. No.: 16/095,486

(22) PCT Filed: Apr. 12, 2017

(86) PCT No.: PCT/EP2017/058767
§ 371 (c)(1),
(2) Date: Oct. 22, 2018

(87) PCT Pub. No.: WO2017/186490
PCT Pub. Date: Nov. 2, 2017

(65) Prior Publication Data
US 2019/0125547 A1 May 2, 2019

(30) Foreign Application Priority Data

Apr. 27, 2016 (GB) .................................. 1607324.9
Jun. 21, 2016 (GB) .................................. 1610820.1

(51) Int. Cl.
*A61F 2/46* (2006.01)
*A61B 90/00* (2016.01)

(52) U.S. Cl.
CPC ............ *A61F 2/4603* (2013.01); *A61B 90/03* (2016.02); *A61B 2090/032* (2016.02); *A61B 2090/0807* (2016.02); *A61B 2090/0811* (2016.02); *A61F 2/4609* (2013.01); *A61F 2/4612* (2013.01);
(Continued)

(58) Field of Classification Search
CPC .................. A61F 2/4609; A61F 2002/4627
See application file for complete search history.

(56) References Cited

U.S. PATENT DOCUMENTS 2,421,354 A * 5/1947 Reiter ...................... A61C 3/08
606/100
2,960,864 A * 11/1960 Watts ...................... H01R 43/26
73/862.01
(Continued)

FOREIGN PATENT DOCUMENTS

EP 549362 A1 6/1993
EP 1190687 A1 3/2002
(Continued)

*Primary Examiner* — Nicholas W Woodall

(57) ABSTRACT

The invention provides an impactor for transmitting an assembly force to a component of an orthopaedic implant. The impactor has first and second telescoping parts which are biased apart by means of a main spring. The main spring is compressed when an assembly force is applied to the parts. An indicator is latched against movement until it is released when the extent of the compression of the main spring by the application of an assembly force exceeds a threshold. The indicator then moves to provide the user with an indication that a minimum assembly force has been applied.

13 Claims, 9 Drawing Sheets

(52) U.S. Cl.
CPC ................ *A61F 2002/4627* (2013.01); *A61F 2002/4681* (2013.01)

(56) References Cited

U.S. PATENT DOCUMENTS

| | | | | |
|---|---|---|---|---|
| 4,919,216 | A | * | 4/1990 | Ikegami .................. B25B 15/06 173/124 |
| 5,282,805 | A | * | 2/1994 | Richelsoph .............. B25D 1/12 606/100 |
| 6,010,508 | A | | 1/2000 | Bradley |
| 6,370,993 | B1 | * | 4/2002 | Pitstick .................. B25B 19/00 173/203 |
| 7,121,165 | B2 | * | 10/2006 | Yamakawa .............. G04D 1/10 81/6 |
| 7,708,739 | B2 | | 5/2010 | Cassell |
| 8,900,245 | B2 | | 12/2014 | Barile |
| 2006/0241631 | A1 | * | 10/2006 | Kilburn ................. A61F 2/4607 606/86 R |
| 2006/0253120 | A1 | * | 11/2006 | Anderson ............ A61B 17/808 606/86 R |
| 2015/0094728 | A1 | * | 4/2015 | Rhoades ............... A61F 2/4609 606/91 |
| 2015/0250614 | A1 | | 9/2015 | Bailey |
| 2016/0184109 | A1 | * | 6/2016 | Davenport ............ A61F 2/4609 606/91 |

FOREIGN PATENT DOCUMENTS

| | | |
|---|---|---|
| EP | 1707160 A1 | 10/2006 |
| FR | 3016281 A1 | 7/2015 |
| WO | WO 1998017210 A1 | 4/1998 |

\* cited by examiner

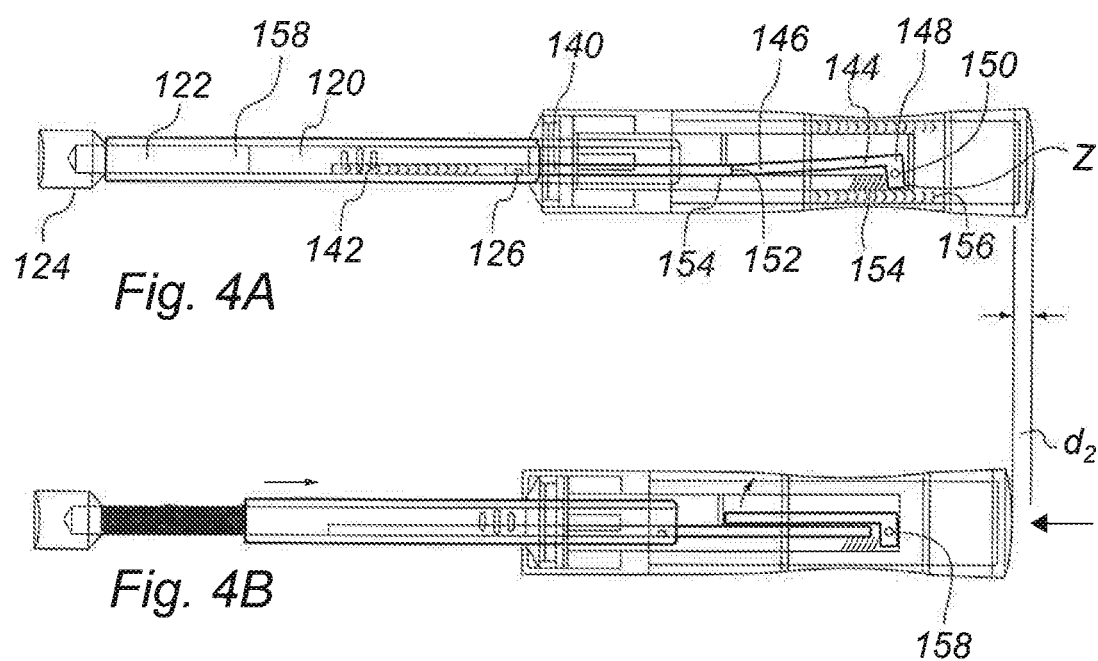

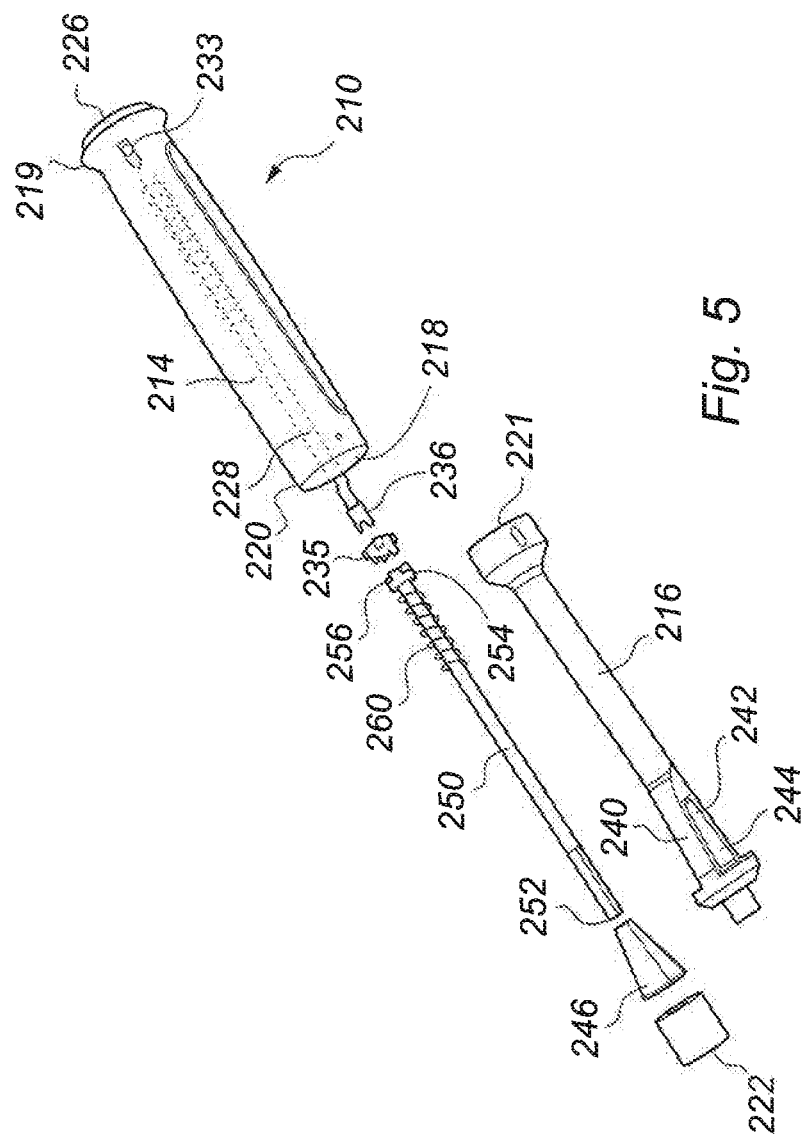

IMPACTOR

CROSS REFERENCE TO RELATED PCT APPLICATION

This application is a National Stage 35 U.S.C. 371 of International Patent Application PCT/EP2017/058767 filed Apr. 21, 2017, which claims priority to United Kingdom Application No. GB1607324.9, filed Apr. 27, 2016 (now abandonded) and GB1610820.1, filed Jun. 21, 2016 (now abandonded), all of which are incorporated by reference in their entireties.

FIELD OF THE INVENTION

The present invention relates to an impactor for transmitting an assembly force to a component of an orthopaedic implant and to a system which includes the impactor.

BACKGROUND TO THE INVENTION

The assembly of many orthopaedic joint prosthesis components requires the application of an assembly force, such as an impaction force. The assembly force can be applied using an impaction instrument such as a hammer, or a tool as disclosed in U.S. Pat. No. 7,708,739. A self-locking taper, such as a Morse taper, is often used to join modular parts of a prosthesis component to one another. An example of a prosthesis component is a femoral component of a hip joint prosthesis which includes a stem part and a head part. The stem part can have a tapered post at its proximal end and the head part can have a tapered bore. The post can be received in the bore.

The force which is applied to parts of a prosthesis component to join them to one another should be sufficient to ensure that the joint is secure. The impactor informs the user that there is no need to apply an additional assembly force.

An assembly force can be applied to a prosthesis component (or part thereof) to implant it in a patient's bone. This can be the case with, for example, a component of a joint prosthesis (for example an acetabular component of a hip prosthesis or a glenoid component of a shoulder prosthesis), or a stem component (for example a femoral component of a hip prosthesis, a humeral component of a shoulder prosthesis, or a femoral component or a tibial component of a knee prosthesis). An impaction force can be applied to implant a prosthesis component, for example using an impaction instrument such as an instrument of the kind discussed above.

U.S. Pat. No. 8,900,245 discloses an impactor for a glenoid component. It discloses an impactor having a shaft which has a bore extending into it. A post is positioned in the shaft and extends from the open end of the bore. The exposed end of the post is threaded and is received in a threaded hole in the glenoid component. A spring is provided between the closed end of the bore and the end of the post which absorbs stresses between the threads of the post and the hole.

U.S. Pat. No. 5,282,805 discloses a surgical mallet in which a spring and sliding shaft arrangement are provided within the head assembly of the mallet. The spring acts as a shock absorber, allowing the end cap of the head assembly to slide axially a predetermined amount. The spring constant can be selected to provide a desired dampening effect. The device limits the force that a prosthesis is subjected to. The mallet can be used to strike an instrument such as a rasp or broach, in which case it might strike the instrument directly. The mallet can be used to apply a force to a component of a prosthesis, in which case the force can be delivered indirectly.

SUMMARY OF THE INVENTION

The invention provides an impactor having first and second telescoping parts which are biased apart by means of a main spring. The main spring is compressed when an assembly force is applied to the parts. An indicator is latched against movement until it is released when the extent of the compression of the main spring by the application of an assembly force exceeds a threshold. The indicator then moves to provide the user with an indication that a minimum assembly force has been applied.

The invention therefore provides an impactor for transmitting an assembly force to a component of an orthopaedic implant, the impactor comprising:

(i) a first member having first and second ends, in which the first end has a surface which is adapted to have an assembly force applied to it, (ii) a second member having first and second ends, in which the first end is adapted to indirectly or directly transmit the assembly force applied to the first member to the component of the orthopaedic implant, in which one of the first and second members has a bore extending within it from its second end which defines a longitudinal axis, and the second end of the other of the first and second members is received in the bore so that one of the first and second member can slide within the bore in a telescoping manner, and in which the impactor includes a main spring acting between the first and second members, the main spring being retained in a compressed condition within the first and second members so that, in the absence of an applied assembly force, it exerts a compression force against the first and second members, and so that an assembly force applied to the first member does not compress the main spring further unless the assembly force exceeds the compression force.

The compression force is the force which is applied by the main spring against the first and second members when it is positioned between the first and second members.

In some constructions the compression force is at least about 1.0 kN. In other constructions the compression force is at least about 1.5 kN, or at least about 2.0 kN, or at least about 2.5 kN, or at least about 3.0 kN, or at least about 3.5 kN, or at least about 4.0 kN. Optionally, the compression force is at least about 50%, or at least about 60%, or at least about 80% of the assembly force. In some constructions the compression force might be not more than about 12 kN. In other constructions the compression force might be not more than about 10 kN, or about 7 kN, or about 5 kN. Optionally, the compression force is at least about 50%, or at least about 60%, or at least about 80% of a threshold assembly force. Optionally, the compression force is not more than about 90%, or not more than about 80%, or not more than about 70%, of a threshold assembly force. For example, in a particular construction of the impactor the compression force can be about 2.5 kN and the threshold assembly force can be about 4.5 kN.

The threshold assembly force is a pre-determined force which is appropriate to achieve secure locking together of two parts of an orthopaedic implant component in order to secure the parts to one another. The parts can be secured to one another by means of a tapered spigot fitting into a tapered bore (a Morse taper). An appropriate threshold assembly force might be at least about 3 kN, for example at least about 4 kN. An appropriate threshold assembly force will often be not more than about 10 kN, for example not more than about 8 kN, especially not more than about 6 kN.

Optionally, the impactor also includes an indicator which can move between first and second positions, the indicator being biased from the first position towards the second position and held in the first position by a latch, and in which the indicator is released from the latch to move towards its second position when the extent of compression of the main spring by the application of an assembly force exceeds a threshold. In some constructions, the threshold of the assembly force is at least about 4.5 kN. This latched indicator provides an additional visual indication to the user that the assembly force has been applied.

According to a further aspect of the invention there is also provided an impactor for transmitting an assembly force to a component of an orthopaedic implant, the impactor comprising:

(i) a first member having first and second ends, in which the first end has a surface which is adapted to have an assembly force applied to it, (ii) a second member having first and second ends, in which the first end is adapted to apply the assembly force directly or indirectly to a component of an orthopaedic implant and thereby to transmit the assembly force applied to the first member to the component of the orthopaedic implant, in which one of the first and second members has a bore extending within it from its second end which defines a longitudinal axis, and the second end of the other of the first and second members is received in the bore so that one of the first and second member can slide within the bore in a telescoping manner, and in which the impactor includes:

(iii) a main spring acting between the first and second members, which is compressed when an assembly force is applied to the first member, through the second member, to the implant component, and (iv) an indicator which can move between first and second positions, the indicator being biased from the first position towards the second position and held in the first position by a latch, and in which the indicator is released from the latch to move towards its second position when the extent of compression of the main spring by the application of an assembly force exceeds a threshold.

Optionally, the main spring is retained in a compressed condition within the first and second members so that it exerts a compression force against the first and second members, and so that an assembly force applied to the first member does not compress the main spring further unless the assembly force exceeds the compression force.

The main spring should be selected so that the extent to which it is compressed when subjected to an assembly force is small when the assembly force is less than the minimum force which is to be applied to an orthopaedic implant component. The compression of the spring when the assembly force is at least equal to the force which is to be applied to the orthopaedic implant should be such that the latch is released as a consequence of relative movement between components of the impactor. Selection of a spring which exhibits appropriate compression behaviour involves selection of a spring with an appropriate spring constant. As is known, the spring constant of a spring depends on several factors including the material from which the spring is made, the treatment of the material, the dimensions of the spring. The main spring will frequently be a helical compression spring. In some constructions, the main spring may be a disc spring (for example, a Belleville spring available from Belville Springs Ltd.), or a spring washer stack (for example, a Belleville washer stack, available from Belville Springs Ltd.), or a pneumatic spring. In some constructions the main spring may be an elastomeric spring.

The assembly force can be applied by an impaction instrument such as a hammer. The assembly force could be applied manually, for example by pressing the first end of the first member.

Preferably, the latch and the indicator are biased towards one another so that they tend to engage one another when the indicator is in its first position, to retain the indicator in the first position until the latch is released. They can be biased towards one another by means of a spring, or another deformable part such as a compressible block of a deformable material such as a rubber.

One of the latch and the indicator can be acted on directly or indirectly by one of the first and second members to release the indicator from the latch, allowing the indicator to move from its first position to its second position. The action against the latch or the indictor member can occur when the extent of compression of the main spring exceeds a threshold when the assembly force applied to the first member exceeds a threshold. The latch or the indicator might be acted on indirectly by one of the first and second members acting through an intermediate part.

The indicator can be provided on the second member and that the latch can be acted directly or indirectly on by the first member.

In some constructions, the latch can move between a first latch position in which it engages the indicator to retain it in its first position and a second latch position in which the indicator is released to move towards its second position.

In some constructions, the latch is biased towards the first latch position. This biasing may be achieved by means of a resiliently deformable part which biases the latch towards the first latch position. Examples of a resiliently deformable part include a spring, and a compressible block of a deformable material such as a rubber.

In addition, in some constructions a resiliently deformable part may be provided which acts on the indicator directly or indirectly to bias it from its first position towards its second position. The extent of deformation of the resiliently deformable part is greater when the indicator is in its first position than when the indicator is in its second position. The direction in which a biasing spring or other resiliently deformable part is deformed can be approximately parallel to the direction of movement of the indicator between its first and second positions.

When the latch is biased towards the first latch position, release of the latch can involve overcoming the biasing force exerted on the latch, for example by a resiliently deformable part such as a spring.

In some constructions, the movement of the indicator between the first and second positions involves movement of the indicator along the second member. For example, in some constructions the indicator moves from its first position towards its second position in a direction from the first end of the first member towards the first end of the second member. The second member is directed towards the component of the orthopaedic implant to which the assembly force is being transmitted. In particular, the second member can be in contact at its first end with the component of the orthopaedic implant when in use. It will therefore frequently be under direct observation by a user. Movement of the indictor in a direction towards the first end of the second member therefore has the advantage that the indictor is moving into the user's field of view, enhancing its visibility to the user.

In some constructions, the indicator moves from its first position towards its second position in a direction from the first end of the second member towards the first end of the first member. This has the advantage that the indicator is moving away from the site of the operation, reducing the likelihood of material (for example soft tissue) being contacted by the indicator as it moves towards its second position.

In some constructions, the movement of the indicator between the first and second positions involves rotation of the indicator around the longitudinal axis. In such constructions, one of the indicator and the latch has at least one tooth and the other of the indicator and the latch has first and second recesses arranged around the longitudinal axis. A recess can be located between two teeth which define the recess. First and second recesses can be defined by first and second teeth which are spaced apart around the indicator or the latch.

The at least one tooth is received in the first recess when the indicator is in its first position, and the at least one tooth is received in the second recess when the indicator is in its second position. A surface of the at least one tooth or a surface of each of the first and second recesses defines a ramp surface which extends around the longitudinal axis and is inclined relative to a plane extending perpendicular to the longitudinal axis. A biasing spring or other resiliently deformable part can urge the surface of the tooth against the surfaces of the recesses. The ramp surface causes the indicator to rotate relative to the latch. It is an advantage of an impactor in which movement of the indicator involves rotation caused by a resiliently deformable part and a ramp surface that the indicator can move between successive latched positions without the impactor having to be reset after each such movement.

Optionally, a resiliently deformable part may be provided which biases the indicator and the latch towards one another. Examples of a suitable resiliently deformable part include a biasing spring and a compressible block of a deformable material such as a rubber. When the movement of the indicator involves rotation about the longitudinal axis of the impactor, it can be preferred that the indicator is biased towards the latch.

In some constructions of the impactor, the movement of the indicator after it has been released from the latch between its first and second positions is substantially independent of the telescopic movement of the second member relative to the first member in response to the application of an assembly force to the first member.

Optionally, the indicator is mounted on the second member, for movement between its first and second positions relative to the second member. The second member is directed towards, especially in contact with, the component of the orthopaedic implant to which the assembly force is being transmitted. It will therefore frequently be under direct observation by a user. Mounting the indicator on the second member therefore has the advantage that it will be visible to the user. It can then be preferred that the movement of the indicator relative to the second member is along or about the longitudinal axis.

Optionally, the impactor includes an inspection portion and the movement of the indicator from its first position to its second position causes the appearance of the inspection portion to change. The inspection portion can be a surface provided on a component of the impactor. For example, the inspection portion can be provided by a surface of the second member. The inspection portion can be a window provided in a component of the impactor. For example, the inspection portion can be a window in the second member. The indicator can move from its first position to its second position so that it becomes visible in the inspection portion when it is in its second position. The indicator can move away from the inspection portion from its first position to its second position so that it is less visible (possibly so that it is not visible) at the inspection portion when it is in its second position. The indicator can move within the inspection portion as it moves from its first position to its second position so that a different portion of the indicator is visible in the inspection portion when the indicator is in its second position compared with when it is in its first position. It can be preferred that the appearance of the inspection portion when the indicator is in its second position contrasts with the appearance of the inspection portion when the indicator is in its first position. For example, the contrast can be provided by surfaces of parts of the impactor having contrasting colours.

The inspection portion can be towards the first end of the second member. This can be advantageous when the first end of the second member contacts a part of an orthopaedic prosthesis component because the inspection portion is in the line of sight of the user of the impactor.

The inspection portion can be in the first member, or towards the second end of the second member (opposite to the first end of the second member). This can be advantageous when the visibility of the first end of the second member is restricted, for example when the impactor is being used to implant a component of an orthopaedic joint prosthesis in a body cavity. This might be the case when the impactor is used for example to implant an acetabular cup component of a hip prosthesis.

In some constructions of the impactor, the first end of the second member is adapted to interface with and thereby directly apply the assembly force to the component of the orthopaedic implant. For example, the first end of the second member may contact a femoral head.

In other constructions of the impactor, the first end of the second member is adapted to interface with an intermediate component which in turn directly contacts the component of the orthopaedic implant. An example of an intermediate component is an alignment guide accessory, such as a femoral head holder.

The invention also provides a system for use in an orthopaedic surgical procedure, which comprises an impactor as herein described and a hammer for applying an assembly force to the first end of the first member.

DETAILED DESCRIPTION OF THE INVENTION

The invention will now be described, by way of example only, with reference to the following drawings, in which:

FIGS. 4a and 4b is a cross-sectional view of the second construction of the impactor along the longitudinal axis B'-B' which show the activation mechanism in pre- and post-activation states.

FIG. 5 is a sectional elevation view of a third construction of an impactor for providing a visual indication to the user that an assembly force has been applied.

Figure 1:
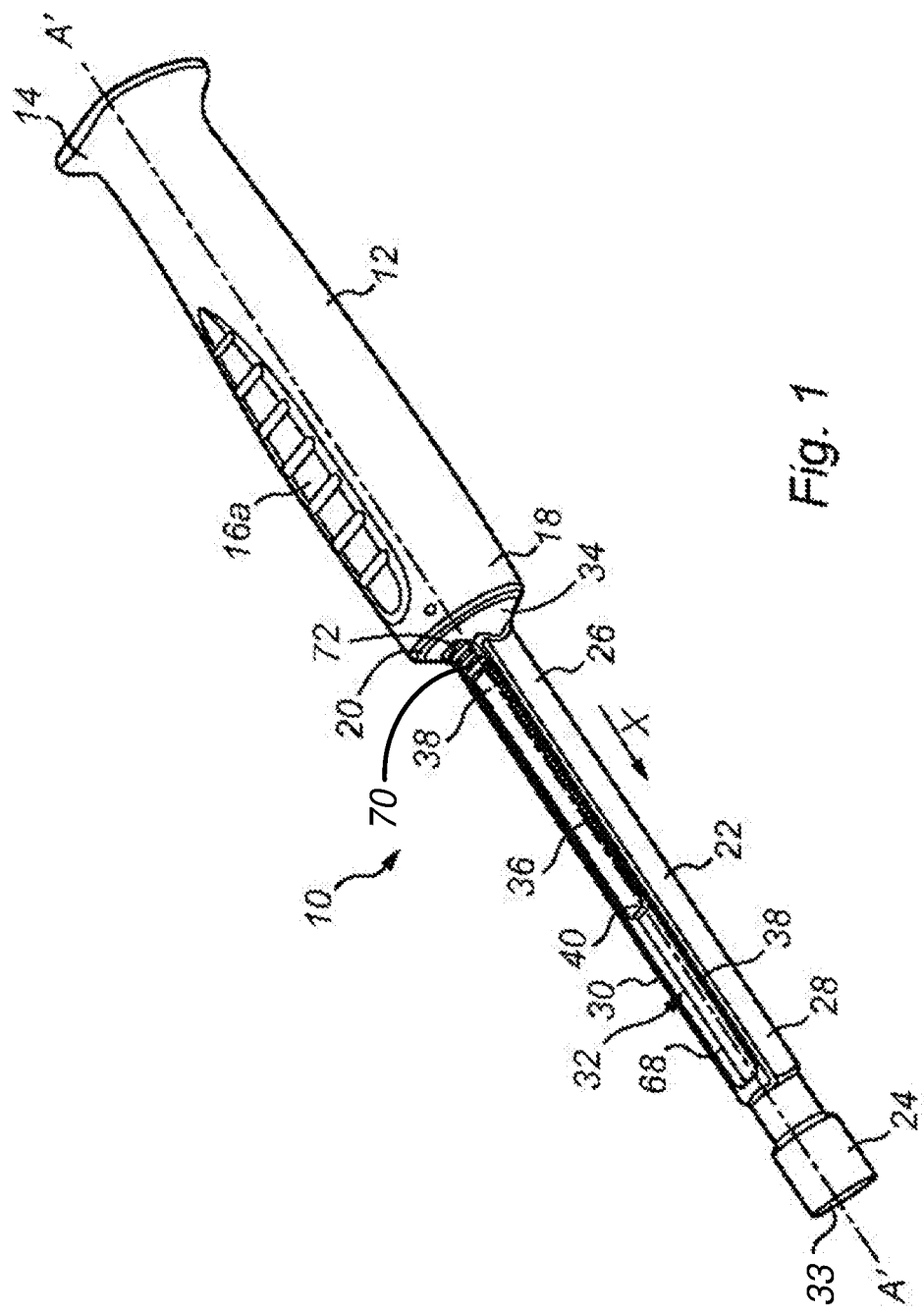
FIG. 1 is a schematic view of a first construction of an impactor for providing a visual indication to the user that an assembly force has been applied.
Figure 2:
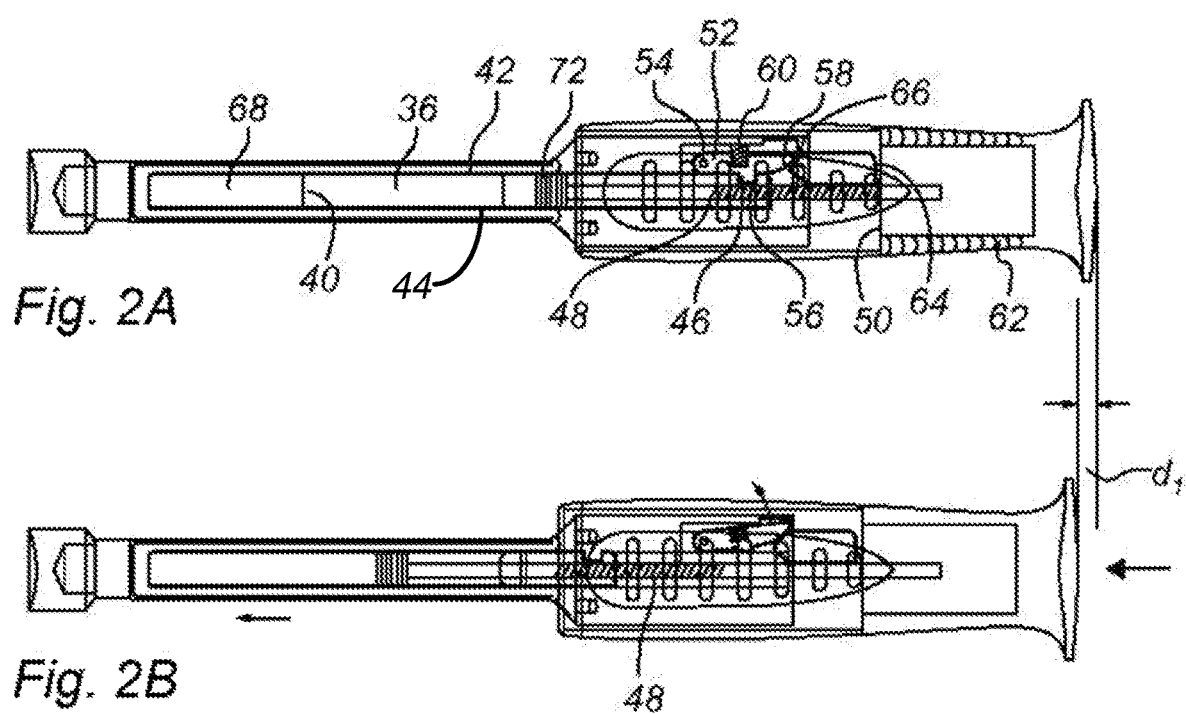
FIGS. 2a and 2b are cross-sectional views of the impactor shown in FIG. 1 along the longitudinal axis A'-A' which show the activation mechanism in pre- and post-activation states.

Referring now to FIGS. 1 and 2, there is shown a first construction of an impactor 10 for providing a visual indication to the user that a minimum assembly force has been applied to the impactor.

The impactor 10 includes a first member in the form of a hollow, elongate handle 12. The handle has a proximal first end 14 and a distal second end 16. A bore 20 is formed in the handle which is open at the distal second end 16.

The proximal first end of the handle is flared outwardly to facilitate application of an assembly force to the handle, for example by means of an impaction instrument such as a hammer. This flared proximal surface provides a larger surface area on to which an impaction instrument such as a hammer can strike the impactor. Alternatively an assembly force might be applied by a user by pressing against the first end of the handle. The handle 12 is provided with at least a first grip region 18 designed to help a user to grip on the impactor. The grip region shown in the drawings includes a plurality of ridges. These ridges may be formed within the material of the handle or applied to the handle.

The impactor includes a second member, in the form of a shaft 22. The shaft 22 has a distal first end 24 and a proximal second end 26 and two guard rails 28, 30 which are arranged parallel to one another and extend between the distal first end 24 and the proximal second end 26. A channel 32 is defined by the distal first end 24, the proximal second end 26 and the two guard rails 28, 30.

A surface 33 of the shaft 22 at its distal first end 24 is configured for either directly engaging the surface of a component of an orthopaedic implant to which an assembly force is to be applied or indirectly contacting a component of an orthopaedic implant via an intermediate component such as an alignment guide. For example, in constructions in which the impactor is for use in applying an assembly force to a convex spherical femoral head, the orthopaedic implant contacting surface has a complementary concave surface.

The proximal second end 26 of the shaft can slide within the bore 18 in the handle in a telescoping manner. The shaft 22 has an annular flange 34 at its proximal second end 26.

The diameter of the annular flange in relation to the diameter of the bore 18 is selected such that sufficient clearance is provided to enable the distal second end 18 of the impactor handle to slide over the flange 34.

The impactor also includes an indicator, in the form of a first generally rectangular shutter 36. The shutter is configured to move between first and second positions within the channel 32. The direction of movement of the shutter from its first position to its second position is from the first proximal end of the first member (i.e., the handle 12) towards the first distal end of the second member (i.e., the shaft 22). FIG. 2a shows the shutter in the first position. FIG. 2b shows the shutter in the second position. The movement of the shutter into the second position provides a visual cue, as a result of the appearance of the shutter into the user's field of view, that the threshold assembly force has been exceeded.

The guard rails 28, 30 reduce the risk that material (for example soft tissue) becomes trapped within the impactor as the shutter slides within the channel 32 into the site of the operation.

The shutter 36 has a proximal end 38, a distal end 40 and two longitudinal opposing edges 42 and 44. A notch 46 is provided along the longitudinal edge 42 adjacent to the proximal end 38. A first compression spring 48, hereinafter referred to as a "biasing spring" acts between the proximal end of the shutter and a stop surface 50 on the second member. This biasing spring biases the shutter from the first position towards the second position.

The impactor also includes a latch 52. The latch is mounted on a pivot pin 54 on the second member adjacent to the longitudinal edge 42 of the shutter 36. The latch has a detent 56 which is complementary in shape to the notch 46. The proximal end of the latch 52 has an angled surface 58. The pivot pin enables pivotal movement of the latch from a first latch position in which the detent 56 is engaged with the notch 46 to a second latch position in which the detent 56 is released from the notch 46.

A latch spring 60 biases the latch 52 in the first latch position (i.e., in which the detent 56 is engaged with the notch 46). In the first latch position the latch 52 constrains the shutter 36 in the first position.

The impactor also includes a second compression spring, hereinafter referred to as the "main spring" 62. The main spring acts between the first member (i.e., the handle 12) and the second member (i.e. the shaft 22) when the second member slides in the bore in the first member in a telescoping manner. A main spring 62 is selected which has a spring constant k which ensures that sufficient assembly force can be transmitted through the first member, the main spring and the second member to a prosthesis component without the spring masking the component from the assembly force by deformation of the spring. For example, the spring constant k can be at least about 3 N/m, or at least about 3.5 N/m or at least about 4 N/m. Optionally, the main spring has a maximum spring constant of not more than about 6 N/m, or not more than about 5.5 N/m, or not more than about 5 N/m. In particular, in constructions of the impactor for use in impacting a femoral head implant, the force spring preferably has a spring constant k of about 4.5 N/m.

The impactor also includes a plunger 64 that extends perpendicularly from the stop surface 50. The plunger has a tapered tip 66. The angle of the tapered tip 66 of the plunger is complementary to the angular surface 58 of the latch.

As shown in FIG. 2b, the handle 12 is caused to move distally over the annular flange 30 by a distance equivalent to the extent of compression, shown as distance "$d_1$," when the extent of the compression of the main spring 62 exceeds a threshold distance. The threshold distance is in the range of about 3 mm to about 6 mm, more preferably about 4 mm to about 5 mm.

The distal movement of the handle 12 causes the stop surface 50, and hence the plunger 64 to move distally by the distance $d_1$. This causes the tapered tip 66 of the plunger 64 to slide against the angular surface 58 of the latch 52. This causes compression of the latch spring 60 and pivoting of the latch 52 from the first latch position to the second latch position. The detent 56 is released from the notch 46 when the latch moves to the second latch position.

Disengagement of the detent 56 from the notch 46 allows the biasing spring 48 to expand, allowing the shutter 36 to move distally from its constrained first position to its second position, which is within the line of sight of the user.

In some constructions, the shaft 22 is also provided with a second slidable shutter (not shown) on an opposing surface of the shaft to the surface on which the first slidable shutter is located. This reduces the risk of the indicator that is provided in the impactor being invisible to the user as a result of the orientation in which the user holds the impactor.

As shown in this construction, the impactor also includes an optional second visual indicator. In the construction shown, this is provided in the form of an inspection surface 68 located within the distal portion of the channel 32. The colour of the inspection surface is selected to contrast highly with the colour of the other parts of the impactor, such as the shaft 22. When the shutter 36 is in the first position the inspection surface 68 is visible to the user. When the shutter 36 is in the second position the inspection surface 68 is concealed by the shutter and is no longer visible to the user. The contrast between the colour of the inspection surface and the colour of the shutter helps to make apparent to the user that the minimal assembly forced has been applied.

The telescoped shaft and handle extend after application to the impactor of a compressing force when the main spring 62 recovers towards its uncompressed length. The shutter is then manually reset from its second position to its first position by the user, where the detent 56 on the latch is received in the notch 46 in the shutter under the action of the latch spring 60. A button 70 is provided on the shutter to help the user to engage the shutter in order to move it towards its first position, against the action of the biasing spring 48, until the button 70 is received in a corresponding cut-out portion 72 at the distal end of the handle.

Figure 3:
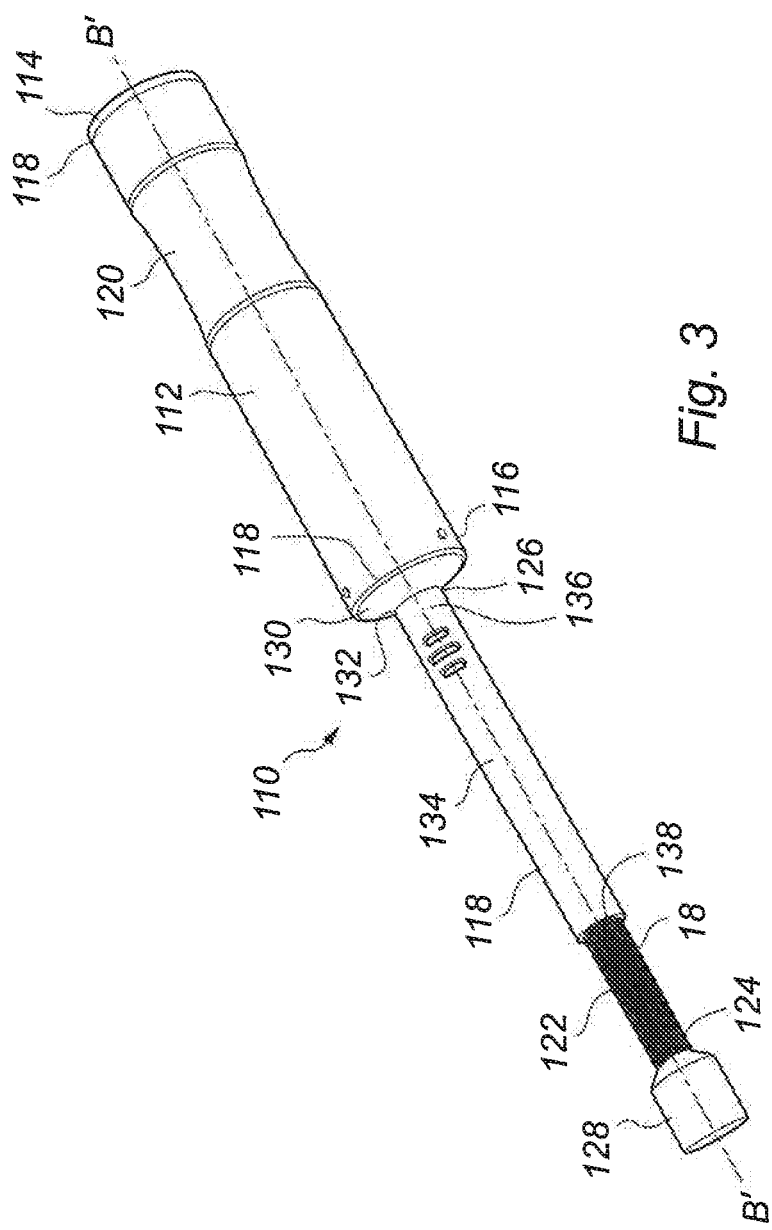
FIG. 3 is a schematic view of a second construction of an impactor for providing a visual indication to the user that an assembly force has been applied.

FIGS. 3 and 4 show a second construction of an impactor 110 for providing a visual indication to the user that a minimum assembly force has been applied to the impactor.

The impactor 110 includes a first member in the form of a hollow, elongate handle 112. The handle has a proximal first end 114 and a distal second end 116. A bore 118 is formed in the handle which is open at the distal end 116.

The handle is ergonomically shaped for single-handed use, and is provided with a waisted portion 120. The outer circumference of the waisted portion is selected to enable a user's hand to be easily wrapped around the handle and to help to locate the handle in the user's hand.

In use, the proximal first end 114 of the handle is hit by a hammer. Although not shown in this construction, the proximal first end 114 can be adapted to facilitate the striking with a hammer. For example, the proximal first end may be flared, thus providing a larger surface area onto which the hammer can strike the impactor.

The impactor includes a second member, in the form of a shaft 122. The shaft 122 has a distal first end 124 and a proximal second end 126.

A surface of the distal first end 124 of the shaft 122 is configured for either directly engaging the surface of a component of an orthopaedic implant to which an assembly force is to be applied or indirectly contacting a component of an orthopaedic implant via an intermediate component such as an alignment guide. For example, in constructions in which the impactor is for use in applying an assembly force to a convex spherical femoral head, the orthopaedic implant contacting surface has a complementary concave surface.

The shaft has an annular flange 130 at its proximal second end 126. The diameter of the annular flange 130 in relation to the diameter of the bore 118 is selected such that sufficient clearance is provided to enable the distal second end 116 of the impactor handle 112 to slide over the flange. The annular flange 130 includes a centrally located bore 132.

The impactor also includes an indicator, in the form of a cylindrical sleeve 134 positioned circumferentially about the shaft 122. The sleeve 134 has a proximal first end 136 and a distal second end 138. An arm 140 extends from the proximal first end 136. A first compression spring 142 hereinafter referred to as a "biasing spring" acts between the shaft 122 and the sleeve 134. This biasing spring biases the sleeve 134 to move from the first position to the second position.

The inner diameter of the sleeve 134 is selected such that there is sufficient clearance between the shaft and the sleeve to the sliding movement of the sleeve along the shaft.

The outer diameter of the sleeve 134 is selected such that sufficient clearance is provided between the sleeve and the bore 132 to enable the proximal first end 136 of the sleeve to slide within the bore 132. In this manner the sleeve can move from a first position to a second position, with the direction of movement being from the first distal end of the second member (i.e., the shaft 122) towards the first proximal end of the first member (i.e, the handle 112). FIG. 4*a* shows the sleeve in the first position. FIG. 4*b* shows the sleeve in the second position. The movement of the sleeve into the second position provides a visual indication that the threshold assembly has been exceeded, when the sleeve moves out of the user's field of view.

The impactor also includes a latch 144. The latch is L-shaped. The latch has a long arm 146 and a short arm 148. The short arm 148 of the latch is mounted on a pivot pin 150 on the internal wall of the sleeve 134. The pivot pin 150 enables pivotal movement of the latch relative to the sleeve from a first latch position in which the free end 152 of the long arm 146 abuts the proximal end 154 of arm 140 to a second latch position in which the free end 152 of the long arm 146 is moved out of an abutting relationship with the proximal end 154 of arm 140.

A latch spring 154 biases the short arm 148 towards the first latch position (i.e., in which the free end 152 of the long arm 146 abuts the proximal 154 end of arm 140). The latch constrains the sleeve 134 in the first position when it is in its first latch position.

The impactor also includes a second compression spring 156, hereinafter referred to as the "main spring". The main spring acts between the first member (i.e., the handle 112) and the second member (i.e., the shaft 122) to cause a telescoping movement between the two members. A main spring 156 is selected which has a spring constant k which ensures that sufficient assembly force can be transmitted through the first member, the main spring and the second member to a prosthesis component without the spring masking the component from the assembly force by deformation of the spring. For example, the spring constant k can be at least about 3 N/m, or at least about 3.5 N/m or at least about 4 N/m. Optionally, the main spring has a maximum spring constant of not more than about 6 N/m, or not more than about 5.5 N/m, or not more than about 5 N/m. In particular, in constructions of the impactor for use in impacting a femoral head implant, the force spring preferably has a spring constant k of about 4.5 N/m.

As shown in FIG. 4b, the main spring 156 is compressed when an assembly force is applied to the impactor. When the assembly force is sufficient to cause the compression of the main spring to exceed a threshold, the handle 112 moves distally over the annular flange 130 by a threshold distance "$d_2$". The threshold distance is in the range of about 3 mm to about 6 mm, more preferably about 4 mm to about 5 mm.

The distal movement of the handle 112 results in a latch contacting surface 158 located within the interior of the handle to be forced distally into contact with the most proximally located surface of the short arm, as indicated at a point Z. The force exerted at point Z is sufficient to compress the latch spring 154 and consequently the latch 144 pivots about the pivot pin 150. The subsequent movement of the long arm 146 of the latch causes the abutting relationship to be disrupted between its free end 152 and the proximal end 148 of arm 140. This allows the compressed biasing spring 142 to recover towards its uncompressed length and as it does so the sleeve 134 is released from its first constrained position and is displaced proximally towards the first end of the first member (i.e. the handle 112) under the force of the biasing spring 142. This has the advantage that the sleeve 134 is moving away from the site of the operation, reducing the likelihood of material (for example soft tissue) being contacted by the sleeve as it moves towards its second position.

The sleeve then reaches its non-constrained second position. In this non-constrained second position the distal end 138 of the sleeve has moved out of the line of sight of the user. In this manner, the user is visually informed that the minimum assembly force has been applied to the impactor.

As shown in this construction, an optional second visual indicator is provided in the form of an inspection surface 158. In the construction shown, this inspection surface 158 consists of a distal portion of the shaft 122 which has a colour that contrasts highly with the colour of the sleeve 134. For example, in a construction in which the sleeve 134 is made of a metal that is silver in colour, the colour of the inspection surface 158 is a contrasting colour such as black. The distal portion of the shaft 122 may be formed of a material of the selected colour. In other constructions, the colour can be applied, in the form of a paint, lacquer, label or laser marking to the distal portion of the shaft 122.

A change in the visibility of the inspection surface 158 as a result of the displacement of the sleeve 134 in the proximal direction provides the user with a second visual indication that the minimum assembly force has been applied. Prior to the proximal displacement of the sleeve 134, the inspection surface 158 is concealed. The proximal displacement of the sleeve 134 results in the inspection surface 158 becoming visible within the line of sight of the user.

After the sleeve has moved from its first position to its second position under the action of the spring 156, it is necessary to reset the impactor for re-use by pulling the sleeve 134 to its first position, thereby compressing the spring. The sleeve is retained in its first position by end long arm 146 of the latch engaging the end surface of arm 140 on the end of the sleeve.

FIG. 5, FIGS. 6a-d and FIG. 7 show a third construction of an impactor 210 for providing a visual indication to the user that a minimum assembly force has been applied to the impactor.

The impactor 210 includes a main body 212 which has a handle portion 214 and a shaft portion 216. The handle portion has a handle bore 218 within it which is open at the first and second ends 219, 220 of the handle portion. The shaft portion has a shaft bore 221 within it which communicates with the bore in the handle portion at the second end of the handle portion. The shaft portion has a surface 222 at its first end which is remote from the handle for either directly contacting a component of an orthopaedic implant or indirectly contacting component of an orthopaedic implant via an intermediate component such as an alignment guide. When the orthopaedic implant has a convex surface, the implant contacting surface at the end of the shaft portion can be concave.

The impactor includes a depressible pusher component 224 which has a button portion 226 and a shaft portion 228. The button portion 226 is a sliding fit in the bore of the handle portion at its first end so that the pusher component and the handle portion can move in a telescoping manner. The pusher component is therefore the first member of the impactor and the main body is the second member of the impactor. The impactor includes a main spring 230 which acts between the pusher component and a ledge 232 in the bore in handle portion 214 of the main body 212.

The movement of the pusher component relative to the handle portion of the main body is defined by a pin 233 which extends between a pair of holes in the wall of the handle portion on opposite sides of the handle portion, through a slot 234 in the pusher component.

The bore 218 in the handle portion 214 of the main body is open at its second end 220. The size of the bore 218 between the ledge 232 and the second end 220 is smaller than the size of the bore between the ledge and the first end 219. The bore has four axially extending teeth 235 provided within it, spaced equally around the bore. The teeth extend from within the bore, and have portions which project beyond the end of the bore.

The shaft portion 228 of the pusher component 224 has four axially extending tines 236 at its free end. The end surfaces of the tines extend helically around the axis of the impactor. The tines are arranged so that they can receive the teeth 235 in the second end 220 of the bore 218 in the handle portion as the button portion 226 of the pusher component is pressed into the bore 218 in the handle portion.

The shaft portion 216 of the main body 212 has a flared portion 240 towards its first end, with the implant contacting surface 222 provided distally of the flared portion. The bore 221 in the shaft portion 216 of the main body opens into a conical chamber 242 within the flared portion 240. Windows 244 are provided in the flared portion. A conical indicator 246 is provided within the conical chamber. The conical indicator has a rectangular bore provided in it at the tip of the indicator.

The impactor includes an indicator shaft 250 within the bore 221 in the shaft portion 216 of the main body 212. The indicator shaft has a spigot 252 at one end with rectangular cross-section which is a sliding fit in the bore in the conical indicator.

The indicator shaft 250 has a circular flange 254 at the end opposite to the spigot end. The exposed surface of the flange has four helical ramps 256 on it.

A biasing spring 260 acts between the circular flange 254 and a ledge 262 in the bore 221 in the shaft portion 216 of the main body 212.

The shaft portion 216 is fastened to the handle portion 214 by means of two pins which extend through aligned holes in the shaft portion and the handle portion. When the shaft portion and the handle portion are connected in this way, the exposed surface of the circular flange 254 on the indicator shaft 252 is urged towards the open end 220 of the bore 218 in the handle portion by the action of the biasing spring 260, so that the portions of the teeth 235 which extend beyond the open end of the bore are engaged by the helical surfaces of the ramps 256. The camming action of the teeth against the helical surfaces of the ramps causes the indicator shaft to rotate within the bore 221 in the shaft portion of the main body. This in turn causes the conical indicator 246 to rotate within the conical chamber in the flared portion of the shaft portion.

The teeth 235 act as a latch to define positions of the indicator shaft 250 relative to the main body 212 of the impactor. The indicator can be released from a first position to move to a second position by means of the tines 236 on the pusher component when the pusher component is moved telescopically within the main body. The tines can fit between the teeth to engage the helical ramps 256. The pusher component is therefore able to displace the indicator shaft axially relative to the shaft portion of the main body as the pusher component moves telescopically in the bore of the main body, as described below with reference to FIGS. 6a to 6d.

The indicator indexing mechanism includes the biasing spring 260, the latch provided by the teeth 235, the indicator shaft 252 and the pusher component 224. Three of the teeth and three of the ramps 256 on the indicator shaft are shown schematically in FIGS. 6a to 6d.

Figure 6A:
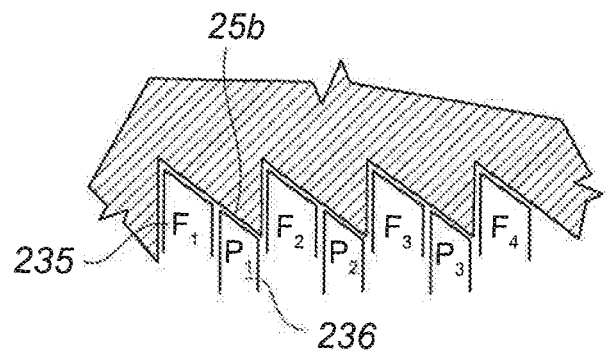
FIG. 6a to 6d is a series of developments of the indicator indexing mechanism within the third construction of the impactor.
Figure 6B:
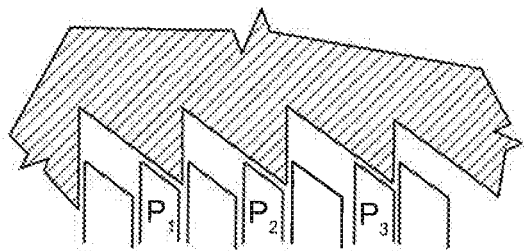

FIG. 6a shows the ramps 256 seated between the teeth 235 at the end of the bore in the handle portion of the main body FIG. 6b shows how the tines 236 extend between the teeth 235 when the pusher component 224 is moved telescopically within the handle portion of the main body, compressing the main spring 230. The helical surfaces on the ends of the tines engage the helical surfaces on the ramps 256 and cause the indicator shaft 252 to be displaced within the shaft portion 216, compressing the biasing spring 260.

Figure 6C:
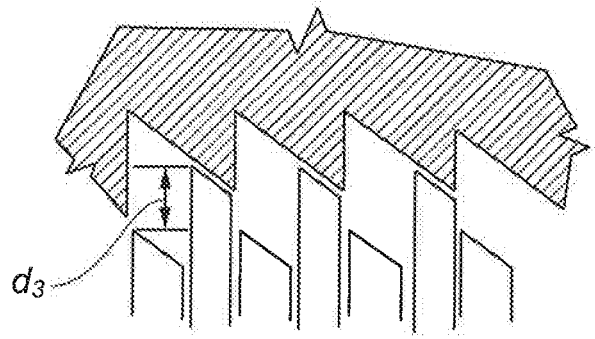

As shown in FIG. 6c, continued movement of the pusher component 224 leads to the formation of an axial gap between the tips of the helical surfaces of the ramps 256 on the indicator shaft and the tips of the teeth 235 where they project beyond the end of the bore in the handle portion of the main body. The formation of an axial gap between the ramps and the teeth occurs when the extent of the compression of the main spring exceeds a threshold corresponding to application of a minimum assembly force to the pusher component relative to the main body. The action of the biasing spring on the indicator shaft, and the camming action of the helical surfaces of the ramps 256 against the surfaces of the tines 236 on the pusher component and the teeth on the handle component, then cause the indicator shaft to rotate within the bore 221 in the shaft portion of the main body. This in turn causes the conical indicator 246 to rotate within the conical chamber in the flared portion of the shaft portion. When there are four teeth and four ramps, each such rotation will be through 90°. Successive depressions of the pusher component give rise to further 90° rotations of the indicator shaft and conical indicator. The conical indicator can have portions of its conical surface provided with contrasting patterns or colours to make it more clear for a user that the indicator has turned within the windows 224. Preferably, the number of such portions of the surface is equal to the number of ramps on the indicator shaft.

Figure 6D:
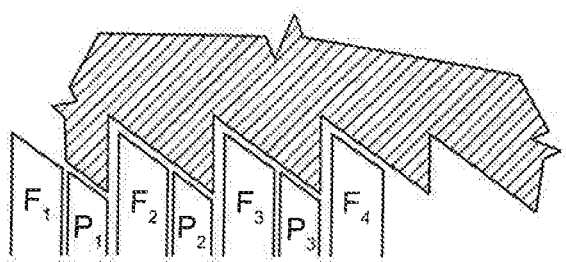
Figure 7:
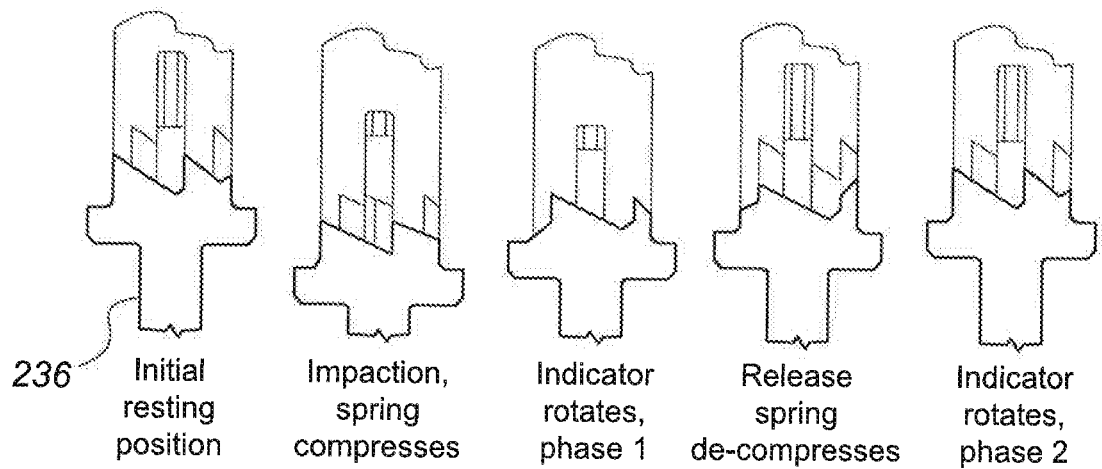
FIG. 7 is a schematic of the indicator indexing mechanism within the third construction of the impactor.

The relative positions of the ramps on the indicator shaft relative to the teeth and the tines after the rotation is shown schematically in FIG. 6d.

The main spring 230 should be selected to have a spring constant k which ensures that sufficient assembly force can be transmitted through the first member, the main spring and the second member to a prosthesis component without the spring masking the component from the assembly force by deformation of the spring. For example, the spring constant k can be at least about 3 N/m, or at least about 3.5 N/m or at least about 4 N/m. Optionally, the main spring has a maximum spring constant of not more than about 6 N/m, or not more than about 5.5 N/m, or not more than about 5 N/m. In particular, in constructions of the impactor for use in impacting a femoral head implant, the force spring preferably has a spring constant k of about 4.5 N/m.

Figure 8A:
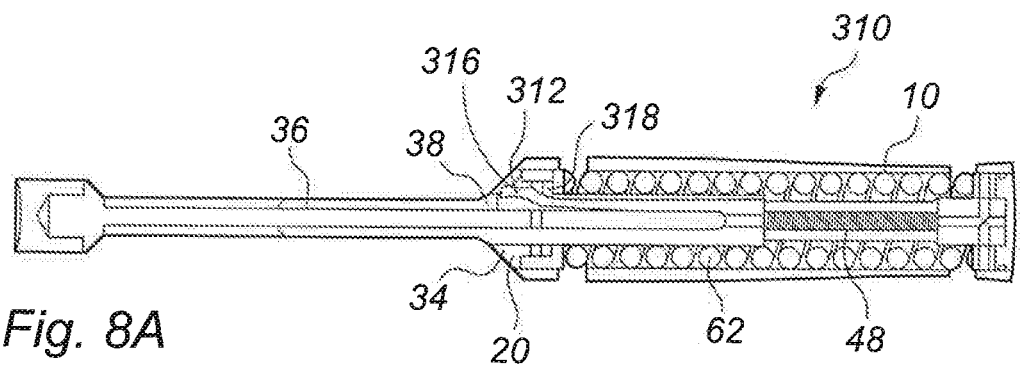
FIGS. 8a to 8c is a longitudinal cross-sectional view of a fourth construction of the impactor which show a leaf-spring based activation mechanism in pre- and post-activation states.
Figure 8B:
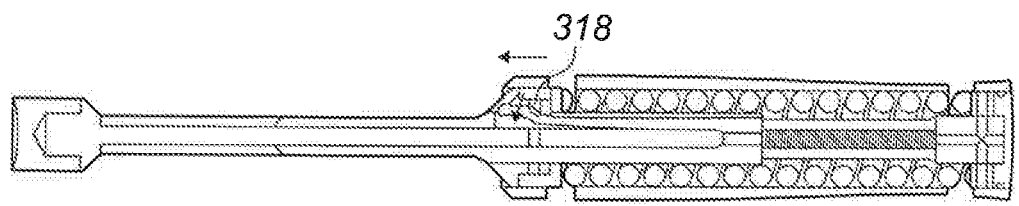
Figure 8C:
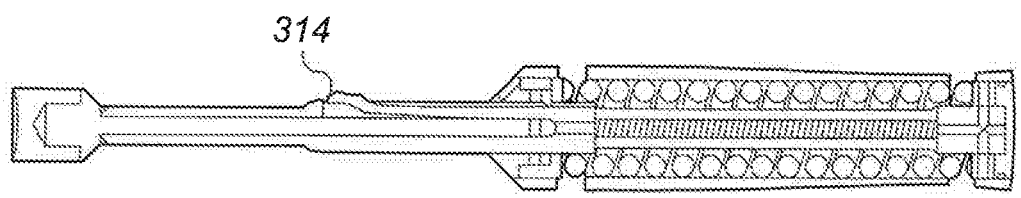

Referring now to FIGS. 8a to 8c, there is shown a third construction of an impactor 310 for providing a visual indication to the user that a minimum assembly force has been applied to the impactor. The impactor is similar in design to the impactor shown in FIG. 1, although in this construction a leaf-spring is used to trigger the movement of the shutter. The same reference numerals used in FIG. 1 will be used for like components in FIGS. 8a to 8c.

The impactor includes a leaf spring 312 mounted in the bore 20 of the handle 10. The leaf spring is located adjacent to the proximal end 38 of the shutter 36. The leaf spring has a distal angled surface 314 that is complementary to the shape of the inner (latch) surface 316 of the annular flange 34. A projection 318 extends inwardly from the inner wall of the bore 20. Projection 318 enables pivotal movement of the leaf spring 212 from a first latch position in which the angled surface 314 is engaged with the latch surface 316 to a second latch position in which the distal angled surface 314 is released from the latch surface.

FIG. 8a shows the impactor in the pre-activation state. Leaf spring 312 is retained in a pre-activation position by its interaction with the latch surface 316.

As shown in FIGS. 8b and 8c, the application of an assembly force that exceeds a threshold causes the handle 12 to move distally over the annular flange 34 by a distance equivalent to the extent of compression, when the extent of the compression of the main spring 62 exceeds a threshold distance. The threshold distance is in the range of about 3 mm to about 6 mm, more preferably 4 mm to about 5 mm.

The distal movement of the handle causes the projection 318 to move in a distal direction, thereby pushing the distal end of the leaf spring inwardly. This causes the pivoting of the leaf spring from the first latch position to the second latch position.

Disengagement of the angled surface 314 from the latch surface 316 allows the biasing spring 48 to expand, allowing shutter 36 to move distally from its constrained first position to its second position, which is within the line of sight of the user.

Figure 9A:
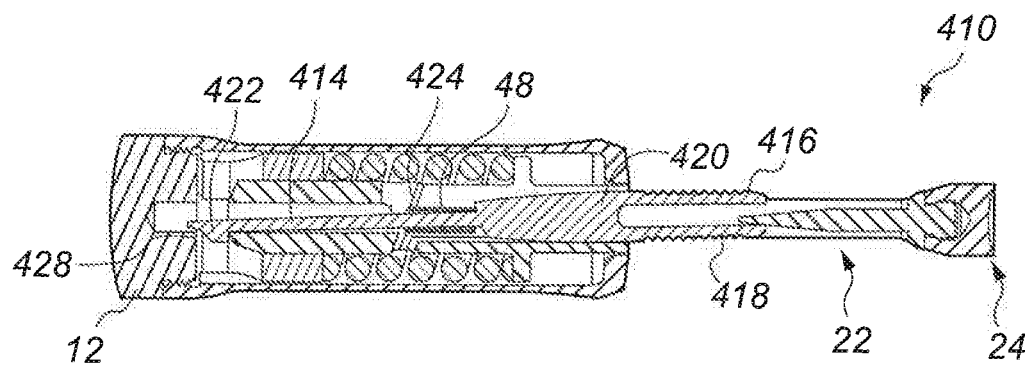
FIGS. 9a to 9c is a longitudinal cross-sectional view of a fifth construction of the impactor which show a tilting rod based activation mechanism in pre- and post-activation states.
Figure 9B:
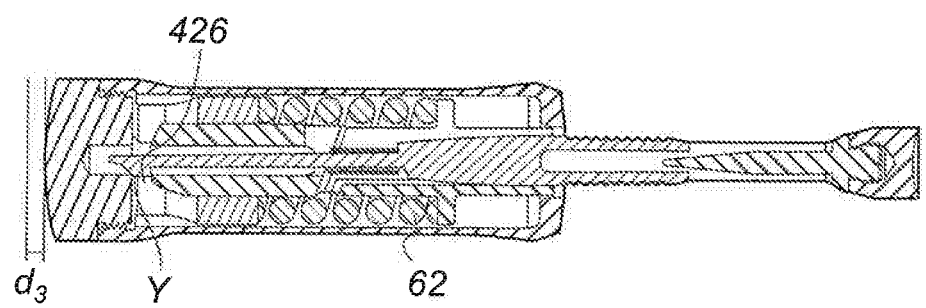
Figure 9C:
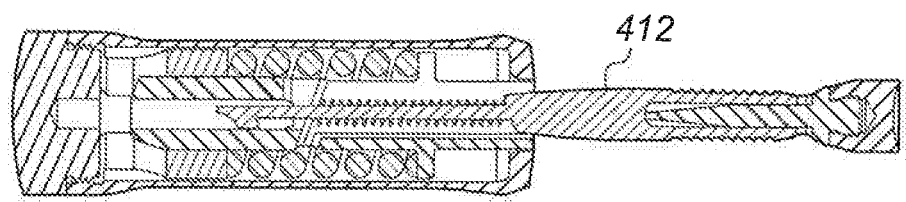

Referring now to FIGS. 9a to 9c, there is shown a fourth construction of an impactor 410 for providing a visual indication to the user that a minimum assembly force has been applied to the impactor. The impactor is similar in design to the impactor shown in FIG. 1, but utilises a tilting-rod activation mechanism to trigger the movement of the shutter. The same reference numerals used in FIG. 1 will be used for like components in FIGS. 9a to 9c.

The shutter 412 includes a proximal elongate neck portion 414 which diverges into two longitudinal opposing arms 416, 418 from a shoulder portion 420. A latch 422 is provided at the proximal end of the neck portion. A first compression spring 48, hereinafter referred to as a "biasing spring", acts between the proximal surface of the shoulder 420 and a stop surface 424 on the second member 22. This biasing spring biases the shutter from the first position towards the second position.

The impactor also includes a notch 426 in the interior of the second member.

As shown in FIGS. 9b and 9c, the main spring 62 is compressed when an assembly force is applied to the impactor. When the assembly force is sufficient to cause the compression of the main spring to exceed a threshold, the handle 12 moves distally over the annular flange by a distance "$d_3$". The threshold distance is in the range of about 3 mm to about 6 mm, more preferably about 4 mm to about 5 mm.

The distal movement of the handle 12 results in a latch contacting surface 428 located in the interior of the handle to be forced distally into contact with the most proximally located surface of latch 422, as indicated at point Y. The force exerted at point Y is sufficient to pivot the latch 422 out of the notch 426. This allows the compressed biasing spring 48 to recover to a less compressed length and as it does so the shutter 412 is released from its first constrained position and is displaced distally towards the distal first end 24 of the second member 22 under the force of the biasing spring 48.

The shutter 412 then reaches its non-constrained second position. In this non-constrained second position the distal end of the shutter has moved into the line of sight of the user. In this manner, the user is visually informed that the minimum assembly force has been applied to the impactor.

The invention claimed is:

1. An impactor for transmitting an assembly force to a component of an orthopaedic implant, the impactor comprising:
    (i) a first member having first and second ends, wherein the first end has a surface which is adapted to have an assembly force applied to it,
    (ii) a second member having first and second ends, wherein the first end is adapted to directly or indirectly transmit the assembly force applied to the first member to the component of the orthopaedic implant,
    wherein one of the first and second members has a bore extending within it from its second end which defines a longitudinal axis, and the second end of the other of the first and second members is received in the bore so that one of the first and second member can slide within the bore in a telescoping manner,
    and wherein the impactor includes a main spring acting between the first and second members, the main spring being retained in a compressed condition within the first and second members,
    and wherein the impactor further comprises an indicator which can move between first and second positions, the indicator being biased from the first position towards the second position and held in the first position by a latch, and wherein the indicator is released from the latch to move towards its second position when the extent of compression of the main spring by the application of an assembly force exceeds a threshold, wherein one of the latch and the indicator is acted on directly or indirectly by one of the first and second members to cause the indicator to be released from the latch to move towards its second position, wherein the latch can move between a first latch position wherein it engages the indicator to retain it in its first position and a second latch position wherein the indicator is released to move towards its second position and the latch is biased towards the first latch position.

2. The impactor of claim 1, wherein the compression force is at least about 1.0 kN.

3. The impactor of claim 1, wherein the movement of the indicator between the first and second positions involves movement of the indicator along the second member.

4. The impactor of claim 3, which includes a resiliently deformable part which acts on the indicator directly or indirectly, biasing it from its first position towards its second position.

5. The impactor of claim 1, wherein movement of the indicator between its first and second positions after it has been released from the latch is substantially independent of movement of the second member relative to the first member in response to the application of an assembly force to the first member.

6. A system for use in an orthopaedic surgical procedure, which comprises an impactor of claim 1 and a hammer for applying an assembly force to the first end of the first member.

7. The impactor for transmitting an assembly force to a component of an orthopaedic implant, the impactor comprising:
    (i) a first member having first and second ends, wherein the first end has a surface which is adapted to have an assembly force applied to it,
    (ii) a second member having first and second ends, wherein the first end is adapted to apply the assembly force directly or indirectly to a component of an orthopaedic implant and thereby to transmit the assembly force applied to the first member to the component of the orthopaedic implant,
    wherein one of the first and second members has a bore extending within it from its second end which defines a longitudinal axis, and the second end of the other of the first and second members is received in the bore so that one of the first and second member can slide within the bore in a telescoping manner,
    and wherein the impactor includes:
    (iii) a main spring acting between the first and second members, and
    (iv) an indicator which can move between first and second positions, the indicator being biased from the first position towards the second position and held in the first position by a latch, and wherein the indicator is released from the latch to move towards its second position when the extent of compression of the main spring by the application of an assembly force exceeds a threshold; and
    wherein one of the latch and the indicator is acted on directly or indirectly by one of the first and second members to cause the indicator to be released from the latch to move towards its second position and wherein the latch can move between a first latch position wherein it engages the indicator to retain it in its first position and a second latch position wherein the indicator is released to move towards its second position and the latch is biased towards the first latch position.

8. The impactor of claim 7, wherein the main spring is retained in a compressed condition within the first and second members so that it exerts a compression force against the first and second members, and so that an assembly force applied to the first member does not compress the main spring further unless the assembly force exceeds the compression force.

9. The impactor of claim 7, wherein the compression force is at least about 1.0 kN.

10. The impactor of claim 7, wherein the movement of the indicator between the first and second positions involves movement of the indicator along the second member.

11. The impactor of claim 10, which includes a resiliently deformable part which acts on the indicator directly or indirectly, biasing it from its first position towards its second position.

12. The impactor of claim 7, wherein movement of the indicator between its first and second positions after it has been released from the latch is substantially independent of movement of the second member relative to the first member in response to the application of an assembly force to the first member.

13. A system for use in an orthopaedic surgical procedure, which comprises an impactor of claim 7 and a hammer for applying an assembly force to the first end of the first member.

* * * * *